United States Patent
Segal

(10) Patent No.: US 6,964,568 B1
(45) Date of Patent: Nov. 15, 2005

(54) DENTAL APPARATUS FOR RECORDING THE INTERDENTAL RELATIONSHIP OF ANTERIOR TEETH

(75) Inventor: Alan J. Segal, Hale (GB)

(73) Assignee: Astek Innovations Limited, Cheshire (GB)

(*) Notice: Subject to any disclaimer, the term of this patent is extended or adjusted under 35 U.S.C. 154(b) by 14 days.

(21) Appl. No.: 10/148,050

(22) PCT Filed: Nov. 24, 2000

(86) PCT No.: PCT/GB00/04471

§ 371 (c)(1),
(2), (4) Date: Aug. 12, 2002

(87) PCT Pub. No.: WO01/37755

PCT Pub. Date: May 31, 2001

(30) Foreign Application Priority Data

Nov. 25, 1999 (GB) .................................... 9927959

(51) Int. Cl.⁷ .............................................. A61C 9/00
(52) U.S. Cl. .......................................... 433/45; 433/38
(58) Field of Search ............................. 433/45, 38, 37, 433/41, 42, 34

(56) References Cited

U.S. PATENT DOCUMENTS

| | | | |
|---|---|---|---|
| 1,584,092 A | 6/1926 | Harris | |
| 2,583,170 A * | 1/1952 | Getz | 433/35 |
| 2,703,452 A * | 3/1955 | Getz | 433/35 |
| 3,045,349 A | 7/1962 | Mars | |
| 3,468,029 A | 9/1969 | Moore | |
| 3,501,837 A | 3/1970 | Clark | |
| 3,978,585 A * | 9/1976 | Holcomb | 433/41 |
| 3,987,548 A | 10/1976 | Jones | |
| 4,204,323 A | 5/1980 | Neubert et al. | |
| 4,449,927 A | 5/1984 | Taylor et al. | |
| 4,459,107 A * | 7/1984 | Weissman | 433/36 |
| 5,297,960 A | 3/1994 | Burns | |
| 5,752,826 A | 5/1998 | Andreiko | |
| 5,820,372 A | 10/1998 | Jones | |
| 6,733,118 B2 * | 5/2004 | Pingrey et al. | 433/38 |

FOREIGN PATENT DOCUMENTS

DE   200 05 383 U   5/2000

\* cited by examiner

Primary Examiner—Melba N. Bumgarner
(74) Attorney, Agent, or Firm—Hollander Law Firm, P.L.C.

(57) ABSTRACT

Dental apparatus for recording the interdental relationship of anterior teeth has an open frame and a handle. A bite tray (9) is secured within the frame so that impression material applied to the bite tray can be readily manipulated between a patient's anterior teeth. The frame may be formed from upper and lower pivotally interconnected arcuate parts (2, 5) and the bite tray (9) has an arcuate segmental body of flexible perforated supporting material with a stiffened strip (10) around its curved periphery. This strip (10) is clamped between confronting faces (15, 16) of the parts (2, 5) and is located in position by engagement of pins (8) on the lower part (2) with holes (11) in the strip (10).

9 Claims, 2 Drawing Sheets

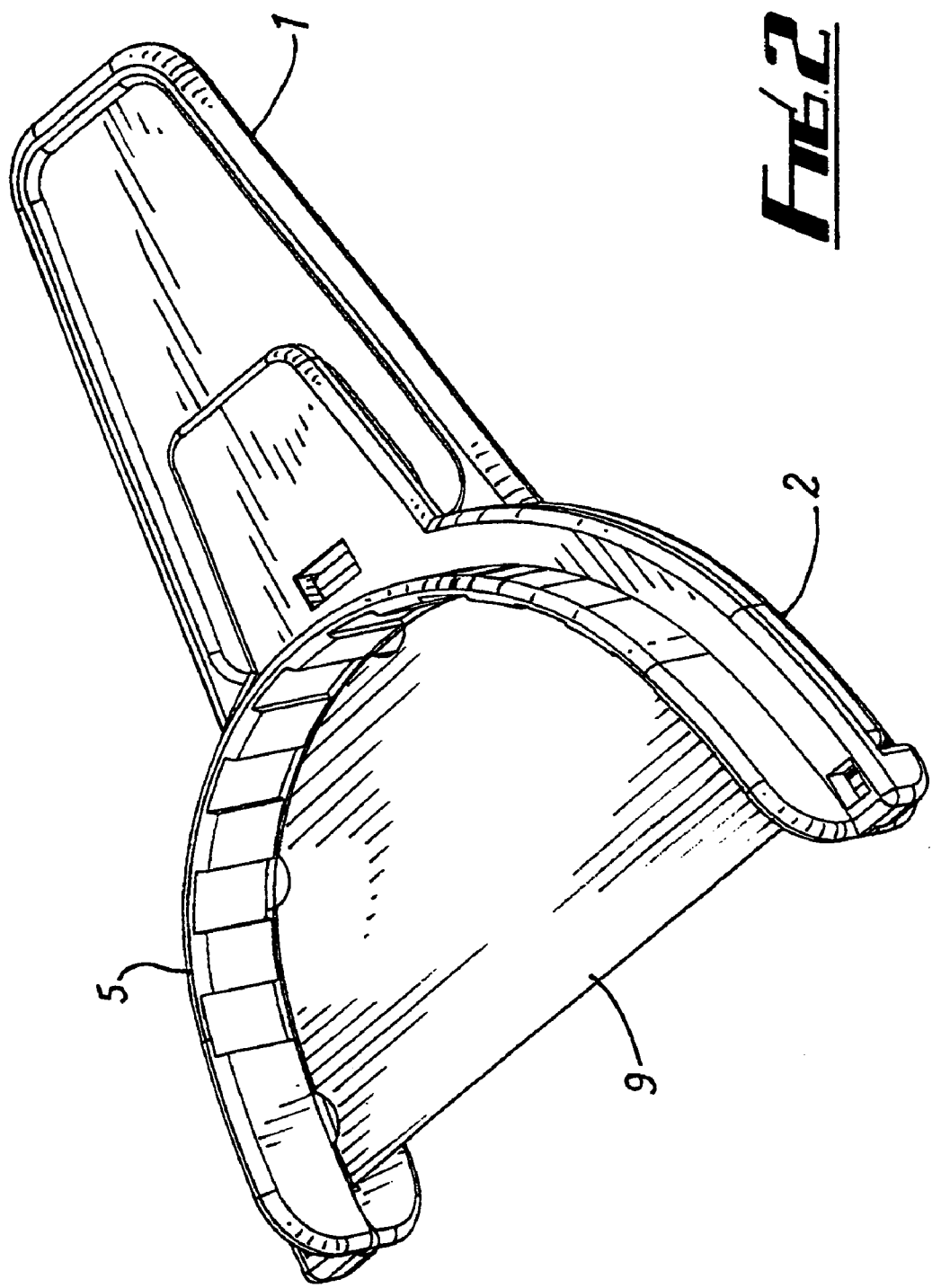

DENTAL APPARATUS FOR RECORDING THE INTERDENTAL RELATIONSHIP OF ANTERIOR TEETH

Figure 1:
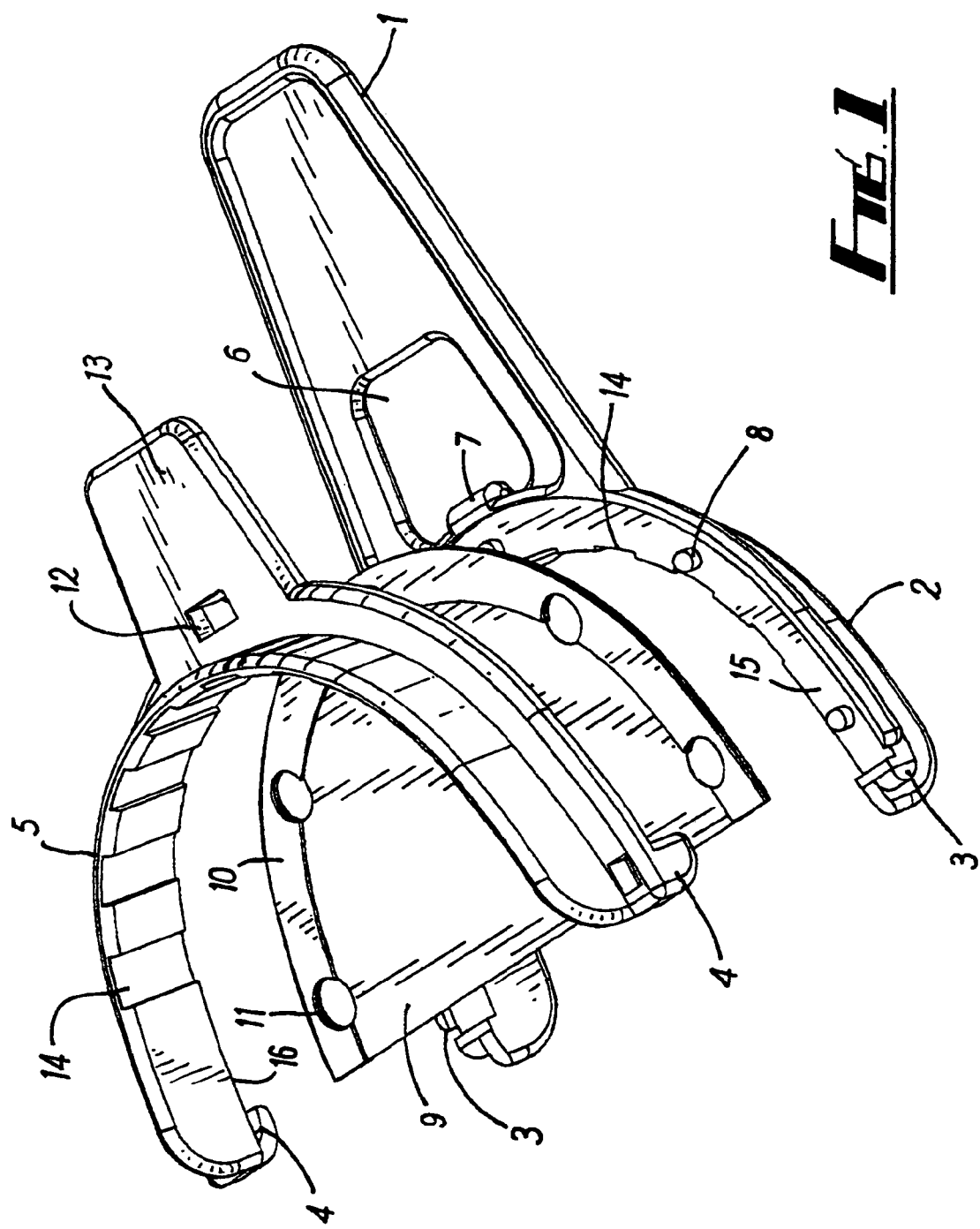

This application is a 371 national stage application of PCT/GB00/04471 filed Nov. 24, 2000, which claims priority of United Kingdom Application No. 9927959.8 filed Nov. 25, 1999.

This invention relates to dental apparatus and, more particularly, to dental apparatus for recording the interdental relationship of teeth, particularly anterior teeth, to assist in the production of dental prosthetics.

In the production of dental prosthetics it is known to use a disposable bite tray which is capable of supporting dental impression material on both its upper and lower sides. In order to record the interdental relationship between upper and lower anterior teeth a bite tray, commonly constructed from a plastic moulded frame with an integral piece of woven textile or plastics gauze material, is coated with dental impression material on both its upper and lower sides and is positioned in a patient's mouth between the anterior teeth. Thereafter the patient bites the bite tray and an impression of the patient's anterior teeth is recorded in the impression material.

With this known arrangement, the impression material-bearing bite tray is difficult to handle. It can be difficult for a person to position the bite tray in the correct position in a patient's mouth, and it can be as difficult to remove the tray after an impression has been taken in so far as the impression material is spread all over the bite tray.

An object of the present invention is to facilitate the handling of anterior bite trays.

According to a first aspect of the present invention therefore there is provided dental apparatus for recording the interdental relationship of anterior teeth, comprising an open supporting frame having a handle and securing means for securing an anterior bite tray within the frame.

With this arrangement, the supporting frame and handle facilitate manipulation of the bite tray when coated with impression material. The impression material-bearing bite tray can be conveniently moved into position between a patient's anterior teeth and, further, after an impression has been taken the tray can be conveniently removed from the patient's mouth.

This is facilitated by the open nature of the frame. That is, the frame has an open side at which an edge of the bite tray is freely exposed for insertion laterally into the patient's mouth. Preferably this open side is wholly or substantially wholly devoid of any part of the frame and is opposite to the handle. This open side may be a straight side.

In a preferred embodiment of the present invention the open frame is substantially arcuate in shape. The handle preferably projects radially from the arcuate frame, particularly from a central region thereof.

The frame may be formed in two parts, an upper part and a lower part, and the securing means may comprise configuration of the two parts between which the bite tray is clamped. A locating arrangement, such as pegs on the frame engageable with holes in the bit tray, may be provided to ensure correct positioning.

The upper and lower parts of the frame may be pivotally interconnected. Preferably pivot joints are provided at end regions of the frame.

In order to clamp the bite tray between the upper and lower parts of the frame a snap-fit arrangement may be provided which allows the parts to be secured in relation to each other. Alternatively, a spring or other fixing may be provided in order to secure the upper and lower parts in relation to each other.

Most preferably, the arrangement is such that the bite tray is removably secured within the frame. The frame may be made from a rigid material such as a plastics material or metal. Preferably, the frame is made from a moulded plastics material. The handle may be formed integrally with the frame and may be formed from the same material on the frame. The material used for the apparatus are preferably such as to allow the apparatus to be autoclavable and, thus, reusable except from the bite tray which is preferably disposed and replaced after each use.

According to a second aspect of the present invention therefore there is provided a bite tray for use with the above described apparatus comprising a body of supporting material substantially of arcuate segmental shape, wherein a peripheral curved edge region of the supporting material is provided with a mounting structure for engagement with the securing means of the frame of the apparatus.

The body of supporting material may comprise flexible material such as a woven textile or plastics gauze material or other perforated structure.

The mounting structure may be arcuate strip-shaped and may be formed from a suitable stiff or self supporting material such as card or plastics material which may be secured to or formed integrally with the body of supporting material.

This mounting structure may be imperforate except for locating holes as mentioned above, although other locating configurations may also be used.

In an alternative embodiment, the bite tray may have a rim or flange of non-perforate material which extends transversely or substantially perpendicularly to the body of supporting material in order to cover or guard at least a part of the frame of apparatus. This advantageously can limit contact between the frame and the impression material so as to facilitate cleaning by autoclaving of the dental apparatus.

According to a third aspect of the invention there is provided a method of recording the interdental relationship of anterior teeth using an anterior bite tray and apparatus comprising an open supporting frame having a handle and securing means for securing the anterior bite tray within the frame wherein the bite tray is secured within the frame by the securing means, impression material is applied to the bite tray, and the bite tray is manipulated between the anterior teeth using the handle.

In one application, the body of supporting material may be pre-impregnated on both sides thereof with a layer of impression material. This may advantageously allow an impression to be taken of the interdental relationship without the need for a full tooth depth impression.

In order that the present invention can be more readily understood a specific embodiment will now be described with reference to the accompanying drawings in which:—

FIG. 1 is a perspective view of one form of dental apparatus according to the invention in an open condition; and FIG. 2 is a perspective view of the arrangement of FIG. 1 in a closed condition ready for use with a bite tray.

Referring to FIG. 1, the dental apparatus has a frame with upper and lower parts and a handle 1 which is integral with the lower part 2. The lower frame part 2 is arcuate in shape and is provided with pivot means 3 at the two ends thereof. The pivot means 3 consist of pegs around which appropriately shaped claws 4 may pivot.

There are two claws 4, one attached to each end of the upper frame part 5. The upper frame part 5 has an arcuate shape which corresponds to the arcuate shape of the lower part 2.

The lower part 2 and upper part 5 are separate from each other and are connected by engagement of the claws 4 with the pivot means 3. Once engaged the facing sides of the parts 2 and 5 are maintained in close proximity to each other by means of a snap-fit arrangement provided at the centre of each of the parts 2 and 5. Both the upper and lower arcuate frame parts 2 and 5 have on their inside vertical surfaces castellations or grooves 14 or other such features which help maintain contact between the impression material and frame before, during and after setting of the impression material.

The handle 1 is a flat, straight elongate structure which projects radially from the centre of the lower part 2 and is tapered away from such part.

The snap-fit arrangement between the parts 2, 5 effected between a flange 7 which extends radially outwardly from the centre of the part 2 within an aperture 6 in the handle 1, and a hook (not shown) which extends downwardly from the centre of the upper part 5. The hook is within the region of a small aperture 12 within a radially outwardly extending straight flat tab 13. The hook is capable of passing over and engaging the flange 7 when the two parts 2 and 5 are in close proximity to each other and the tab 13 overlies the aperture 6 in the handle 1, thereby to secure the parts 2, 5 against each other.

The parts 2 and 5 and the handle 1 and the tab 13 are all made from an extruded plastics material. This material has sufficient inherent resiliency to allow the hook and flange 7 to be readily separated from, and engaged with, each other as required.

The lower part 2 is further provided with several upwardly extending integral moulded plastics pins 8. These pins correspond with dimples (not shown) on the facing side of the upper part 5.

The dimples are able to receive the pins 8 to enable the parts 2 and to be placed in close proximity to each other.

The purpose of the pins 8 is to provide a means by which an anterior bite tray 9 can be located relative to the lower part 2 prior to being clamped between the upper and lower parts 5 and 2.

The bite tray 9 as used with the apparatus consists of an arcuate segmental body of perforated material (woven textile or plastics gauze or other perforate material) which has attached along its curved edge a correspondingly curved piece of flat card 10. The card 10 is provided with several holes 11 therethrough which correspond in shape and location to the pins 8 of the lower part. Consequently the holes 11 of the bite tray 9 can be lined up with the pins 8, thus, allowing the bite tray 9 to be engaged with the lower part 2 by passing the pins 8 through the holes 11.

Thereafter, the bite tray 9 can be secured between the upper and lower parts 5 and 2 by engaging the claws 4 and pivot means 3 and then forcing the hook over the flange 7 and, therefore, securing the lower and upper parts 2 and 5 in close proximity to each other whilst clamping the bite tray there between.

The bite tray 9 is therefore secured in position by clamping between confronting flat faces 15, 16 of the upper and lower parts 2, 5, the pins 8 acting to locate the bite tray 9 and the snap-fit arrangement 7 acting as a releasable lock.

In operation, once a bite tray has been clamped, as shown in FIG. 2, between the lower and upper parts 2 and 5, dental impression material (not shown) is applied to both sides of the bite tray 9. Once a sufficient quantity of impression material is applied the operator may grip the handle 1 and manipulate the instrument into a patient's mouth so that the impression material is in position between the anterior teeth for which an impression is desired. The frame defined by the parts 2 and 5 is of arcuate, open configuration having an open front edge opposite the handle 1 at which the straight (chordal) edge of the segmental bite tray body material is exposed, slightly inset relative to the free ends of the parts 2, 5. The frame therefore permits easy insertion of the impression material-bearing bite tray into the patient's mouth between the anterior teeth.

Once an impression has been made in the impression material the operator can, conveniently, remove the apparatus from the patient's mouth by manipulating the handle 1. After the impressioned material on the bite tray 9 has served its purpose parts 2 and 5 may then be separated from each other and the bite tray removed and the impression material-bearing bite tray is discarded whilst the apparatus is retained and autoclaved for future use.

It is to be understood that the above described embodiment is by way of illustration only.

What is claimed is:

1. Dental apparatus for recording the interdental relationship of anterior teeth, comprising:
    an open substantially arcuate supporting frame having a handle and which is formed in upper and lower frame parts;
    an anterior bite tray comprising a body of supporting material;
    a mounting structure applied to a peripheral curved edge region of the body of supporting material;
    securing means for securing the anterior bite tray within the supporting frame, wherein the securing means comprises configurations of the upper and lower frame parts between which the mounting structure is clamped; and
    a locating arrangement for locating the bite tray relative to the upper and lower frame parts which comprises pins on the upper and lower frame parts engageable with holes in the bite tray.

2. Dental apparatus according to claim 1 wherein the handle projects radially from the arcuate frame.

3. Dental apparatus according to claim 2 wherein the handle projects from a central region of the arcuate frame.

4. Dental apparatus according to claim 1 wherein the handle is formed integrally with the frame.

5. Dental apparatus for recording the interdental relationship of anterior teeth, comprising:
    an open substantially arcuate supporting frame having a handle and which is formed in upper and lower frame parts, wherein the upper and lower frame parts are pivotally interconnected;
    an anterior bite tray comprising a body of supporting material;
    a mounting structure applied to a peripheral curved edge region of the body of supporting material; and
    securing means for securing the anterior bite fray within the supporting frame, wherein the securing means comprises configurations of the upper and lower frame parts between which the mounting structure is clamped.

6. Dental apparatus according to claim 5 wherein the upper and lower frame parts are pivotally interconnected by pivot joints provided at end regions of the frame.

7. Dental apparatus for recording the interdental relationship of anterior teeth, comprising:

an open substantially arcuate supporting frame having a handle and which is formed in upper and lower frame parts;

an anterior bite tray comprising a body of supporting material;

a mounting structure applied to a peripheral curved edge region of the body of supporting material;

securing means for securing the anterior bite tray within the supporting frame, wherein the securing means comprises configurations of the upper and lower frame parts between which the mounting structure is clamped; and a snap-fit arrangement to secure the upper and lower frame parts relative to each other.

8. Dental apparatus according to claim 7, wherein the snap-fit arrangement comprises:

a flange extending radially outward from a center of the lower frame part within an aperture in the handle; and a hook extending downwardly from a radially extending outward tab of the upper frame part.

9. Dental apparatus for recording the interdental relationship of anterior teeth, comprising:

an open substantially arcuate supporting frame having a handle, said frame comprising upper and lower frame parts;

an anterior bite tray comprising a body of supporting material; and a mounting structure applied to a peripheral curved edge region of the body of supporting material, wherein the mounting structure comprises a stiff arcuate strip fixed to the supporting material and has holes to receive locating pins of the frame; and a snap-fit arrangement to secure the upper and lower frame parts relative to each other, wherein the upper and lower frame parts clamp the mounting structure to secure the anterior bite tray within the supporting frame.

* * * * *